United States Patent
Cruz-Acosta et al.

(10) Patent No.: US 9,669,122 B1
(45) Date of Patent: Jun. 6, 2017

(54) ULTRAVIOLET LIGHT-BASED DISINFECTING CABINET

(71) Applicants: Ramiro Cruz-Acosta, Kissimme, FL (US); Jaslier Cruz, Kissimme, FL (US); Roberto Muniz, Kissimme, FL (US)

(72) Inventors: Ramiro Cruz-Acosta, Kissimme, FL (US); Jaslier Cruz, Kissimme, FL (US); Roberto Muniz, Kissimme, FL (US)

(*) Notice: Subject to any disclaimer, the term of this patent is extended or adjusted under 35 U.S.C. 154(b) by 113 days.

(21) Appl. No.: 14/829,064

(22) Filed: Aug. 18, 2015

(51) Int. Cl.
*A61L 2/10* (2006.01)
*A45D 44/00* (2006.01)

(52) U.S. Cl.
CPC .............. *A61L 2/10* (2013.01); *A45D 44/00* (2013.01)

(58) Field of Classification Search
USPC ........................................ 250/455.11, 453.11
See application file for complete search history.

(56) References Cited

U.S. PATENT DOCUMENTS

| | | | |
|---|---|---|---|
| 3,433,579 A * | 3/1969 | Runnion | A61L 2/10 250/455.11 |
| 3,447,892 A * | 6/1969 | Keith | A61L 2/10 128/898 |
| 3,500,840 A * | 3/1970 | Maatz | A61L 2/00 134/111 |
| 3,547,578 A | 12/1970 | Eppler | |
| 4,786,812 A | 11/1988 | Humphreys | |
| 4,896,042 A | 1/1990 | Humphreys | |
| 6,242,753 B1 | 6/2001 | Sakurai | |
| 2,554,156 A1 | 9/2005 | Bret Ja Chisholm | |
| D655,125 S | 3/2012 | Turner | |
| 8,506,195 B2 | 8/2013 | Diaz | |
| 2013/0198991 A1 | 8/2013 | Cadigan | |
| 2014/0096801 A1 | 4/2014 | McCormick | |

FOREIGN PATENT DOCUMENTS

WO   WO2009065128   8/2009

* cited by examiner

*Primary Examiner* — Kiet T Nguyen

(57) ABSTRACT

The ultraviolet light based disinfecting cabinet is designed to be used by hair styling salons and barbershops as a replacement for dry cabinet disinfection. The ultraviolet light based disinfecting cabinet operates in a manner similar to dry cabinet disinfection but instead of the heat used in the dry cabinet disinfection method ultraviolet light is used for disinfecting the grooming tools typically used in hair styling salons and barbershops. The ultraviolet light based disinfecting cabinet comprises a cabinet and an ultraviolet disinfection system.

19 Claims, 3 Drawing Sheets

ULTRAVIOLET LIGHT-BASED DISINFECTING CABINET

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of cabinets for laboratory, dental, barber, or medical uses, more specifically, a cabinet with ultraviolet disinfection.

SUMMARY OF INVENTION

The ultraviolet light based disinfecting cabinet is designed to be used by hair styling salons and barbershops as a replacement for dry cabinet disinfection. The ultraviolet light based disinfecting cabinet operates in a manner similar to dry cabinet disinfection but instead of the heat used in the dry cabinet disinfection method ultraviolet light is used for disinfecting the grooming tools typically used in hair styling salons and barbershops.

These together with additional objects, features and advantages of the ultraviolet light based disinfecting cabinet will be readily apparent to those of ordinary skill in the art upon reading the following detailed description of the presently preferred, but nonetheless illustrative, embodiments when taken in conjunction with the accompanying drawings.

In this respect, before explaining the current embodiments of the ultraviolet light based disinfecting cabinet in detail, it is to be understood that the ultraviolet light based disinfecting cabinet is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the ultraviolet light based disinfecting cabinet.

It is therefore important that the claims be regarded as including such equivalent construction insofar as they do not depart from the spirit and scope of the ultraviolet light based disinfecting cabinet. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
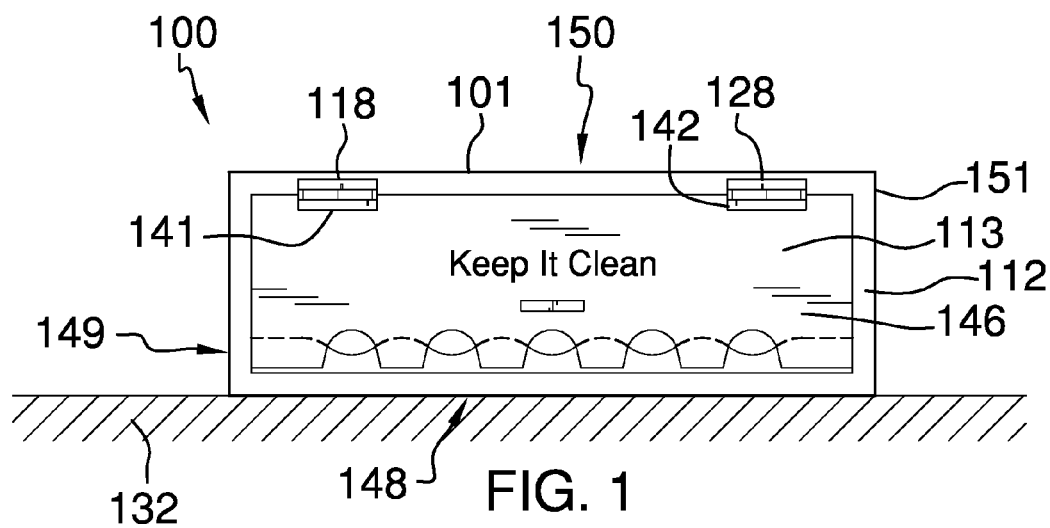
FIG. 1 is a front view of an embodiment of the disclosure.
Figure 2:
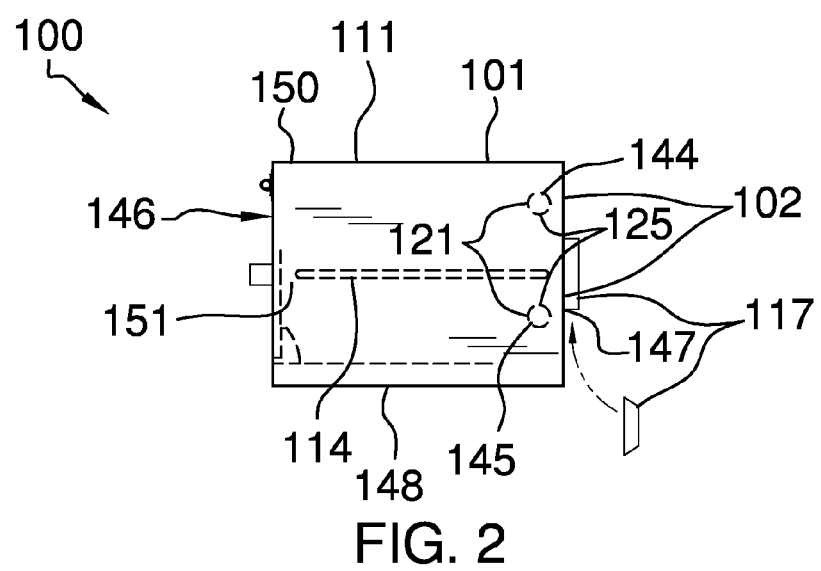
FIG. 2 is a side view of an embodiment of the disclosure.
Figure 3:
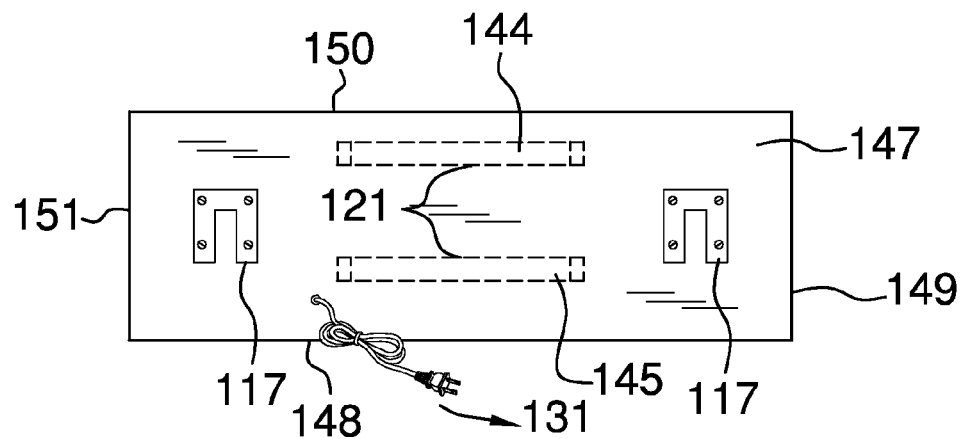
FIG. 3 is a back view of an embodiment of the disclosure.
Figure 4:
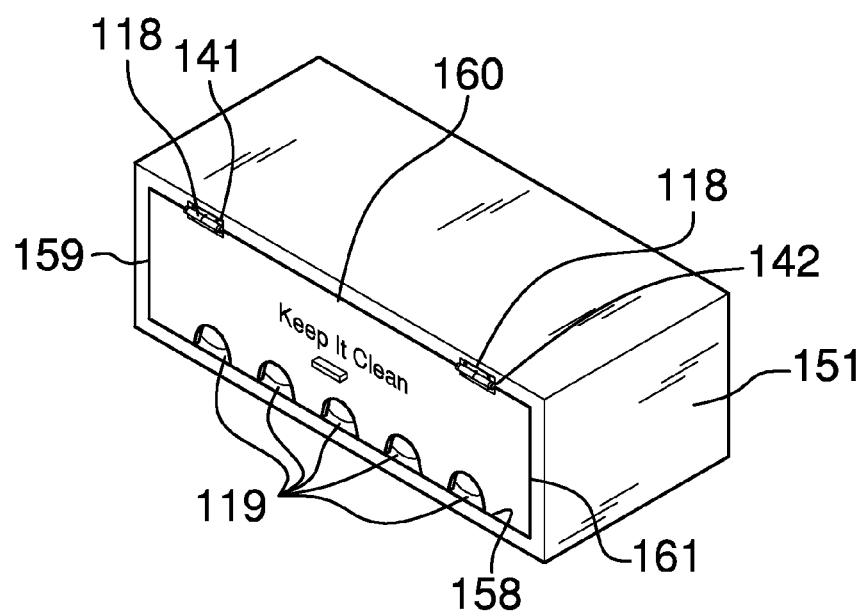
FIG. 4 is a perspective view of an embodiment of the disclosure.
Figure 5:
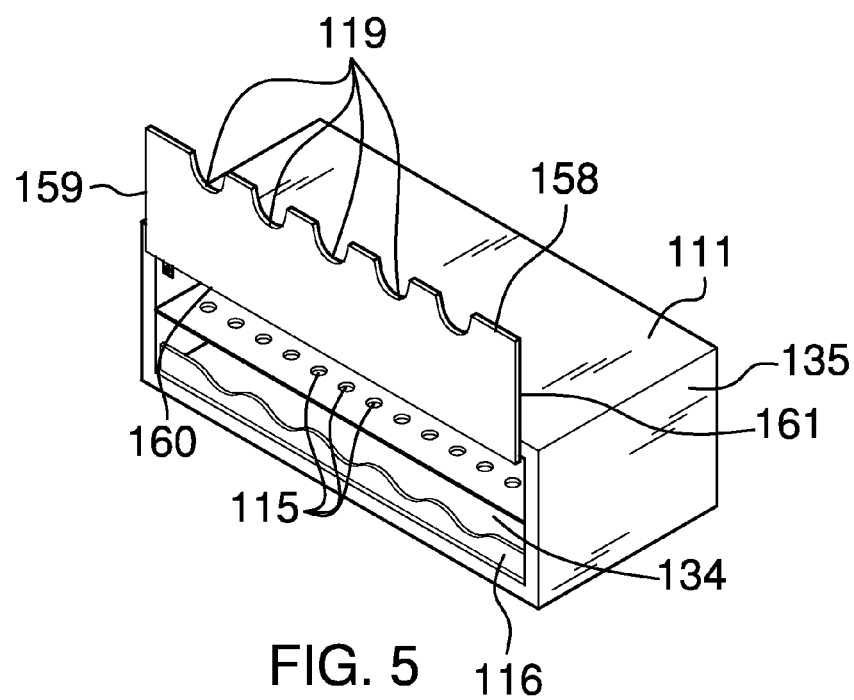
FIG. 5 is a perspective view of an embodiment of the disclosure.
Figure 6:
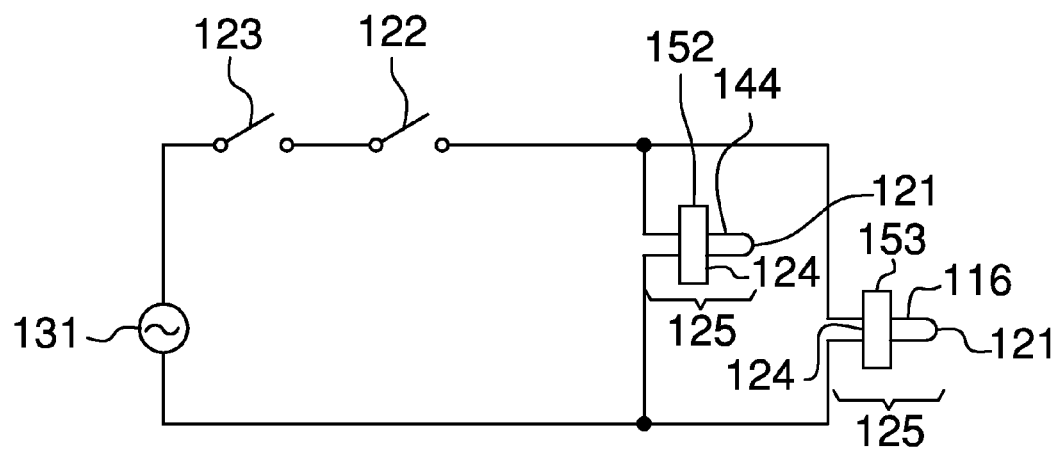
FIG. 6 is a schematic view of an embodiment of the disclosure.

Detailed reference will now be made to a first potential embodiment of the disclosure, which is illustrated in FIGS. 1 through 6. The ultraviolet light based disinfecting cabinet 100 (hereinafter invention) comprises a cabinet 101 and an ultraviolet disinfection system 102.

The cabinet 101 is a piece of furniture in the form of a rectangular block that is used to contain the items that are to be disinfected. The cabinet 101 can be wall mounted or can stand alone. The cabinet 101 comprises a box 111, a front frame 112, a door 113, a tray 114, a plurality of holes 115, a rubber molding 116, a wall mount 117, and one or more hinges 118. The cabinet 101 is further defined with a first side 146, a second side 147, a third side 148, a fourth side 149, a fifth side 150, and a sixth side 151. The front frame 112 and the door 113 are externally mounted on the first side 146 of the cabinet 101. The second side 147 of the cabinet 101 is the side distal from the first side 146 of the cabinet 101. The third side 148 of the cabinet 101 is designed to rest on a supporting surface 132. When facing the first side 146 of the cabinet 101, the names of the remaining sides, in order moving counter clockwise from the third side 148 of the cabinet 101, are the fourth side 149, the fifth side 150, and the sixth side 151.

The box 111 is a single unit that forms the second side 147, the third side 148, the fourth side 149, the fifth side 150, and the sixth side 151 of the cabinet 101. The front frame 112 is a structural component attached to the first side 146 of the box 111 and upon which the door 113 is mounted. The door 113 is a board or plank that is sized to cover the first side 146 of the cabinet 101. The door 113 is mounted to the front frame 112 using the one or more hinges 118. The door 113 is mounted such that when opening the door 113, the door 113 swings from the third side 148 of the cabinet 101 towards the fifth side 150 of the cabinet 101. The door 113 is further defined with a first edge 158, a second edge 159, a third edge 160, and a fourth edge 161. The first edge 158 is proximal to the third side 148 of the box 111. The second edge 159 is proximal to the fourth side 149 of the box 111. The third edge 160 is proximal to the fifth side 150 of the box 111. The fourth edge 161 is proximal to the sixth side 151 of the box 111.

The first edge 158 of the door 113 is formed with a plurality of semicircular cut outs 119. The purpose of the plurality of semicircular cut outs 119 is to allow the cables associated with the grooming tools typically used in hair styling salons and barbershops to be easily placed within the cabinet 101. This cable way allows the grooming tools typically used in hair styling salons and barbershops to be charged while the grooming tools typically used in hair styling salons and barbershops are being disinfected. A rubber molding 116 is installed on the front frame 112 near the eighteenth side 158 of the door 113. The purpose of the rubber molding 116 is to contain the ultraviolet c radiation generated with the case and prevent the escape of the ultraviolet c radiation from the cabinet 101 through the plurality of semicircular cut outs 119.

The tray 114 is a shelf that is mounted inside the cabinet 101. The tray 114 has formed in it a plurality of holes 115. The purpose of the plurality of holes 115 is to act as a receptacle to receive a grooming tool and hold the grooming tool in a suitable position for disinfection.

Mounted on the seventh side 147 inside the box 111 is the ultraviolet disinfection system 102. The ultraviolet disinfection system 102 further comprises a plurality of ultraviolet lights 121, a door switch 122, a master switch 123 and a plurality of ballasts 124. Each of the plurality of ultraviolet lights 121 comprises an ultraviolet c light bulb. Each of the plurality of ultraviolet lights 121 are mounted in a ballast selected from the plurality of ballasts 124 that are mounted on the seventh side 147 of the box 111. The purpose of each of the each ballast selected from the plurality of ballasts 124 is to regulate the current flow and voltage to insure that it is sufficient to start and operate each of the plurality of ultraviolet lights 121. Each individual combination of ballast and ultraviolet c light 125 is mounted on the seventh side 147 of the box 111 in such a way that the interior of the box 111 is completely illuminated with ultraviolet c radiation. Each of the plurality of ballasts 124 are powered by from the national electrical grid 131. The operation of the each of the plurality of ballasts 124 is controlled by a master switch 123, and a door switch 122. The master switch 123 controls the flow of electrical power into the cabinet 101 and to each of the plurality of ballasts 124. The door switch 122 is an interlock switch that prevents the operation of the plurality of ballasts 124 when the door 113 is opened. This is shown most clearly in FIG. 6.

To use the invention 100, the cabinet 101 is plugged into the national electrical grid 131 and the master switch 123 is turned on. Once the door 113 is closed, the grooming tools typically used in hair styling salons and barbershops are bathed in a disinfecting light of ultraviolet c radiation. If the master switch 123 is turned off, or the door 113 is opened, the disinfecting light of ultraviolet c radiation is turned off.

In the first potential embodiment of the disclosure, the cabinet 101 used is commercially available. The door 113 is fitted on the front frame 112 using a first hinge 141 and a second hinge 142. The plurality of ultraviolet lights 121 comprises a fourth ultraviolet c light 144 and a fifth ultraviolet c light 145. The plurality of ballasts 124 further comprises a twelfth ballast 152 and a thirteenth ballast 153. The fourth ultraviolet c light 144 is placed in the twelfth ballast 152 mounted above the tray 114. The fifth ultraviolet c light 145 is placed in the thirteenth ballast 153 mounted below the 114 tray. The fourth ultraviolet c light 144 and the fifth ultraviolet c light 145 are readily and commercially available fluorescent ultraviolet C lights that covers the 248 to 262 nm range. The ballasts and switches required to operate the UV lights are commercially available. The wall mount 117 comprises commercially available lumber and hardware used to mount the cabinet 101 on the wall. Methods to mount cabinets to walls are well known and documented in the art.

The following definitions were used in this disclosure:

Door Switch: As used in this disclosure, a door switch is and electrical contact device that is attached to a door/door frame and is operated by opening and closing the door.

Dry Cabinet Disinfection: As used in this disclosure, dry cabinet disinfection is a cabinet that is used to disinfect items that are placed within the chamber of the cabinet wherein hot air with minimal water content disinfects items placed within the chamber of the cabinet through heat conduction between the hot air and items placed within the chamber of the cabinet Ultraviolet Light: As used in this disclosure, ultraviolet light is understood to be electromagnetic radiation with a wavelength lesser than visible light. In general usage, ultraviolet light is taken to mean electromagnetic radiation with a wavelength less than 400 nm.

Ultraviolet C Light: As used in this disclosure, ultraviolet C light is understood to be ultraviolet light with wavelengths in the range of 200 nm to 300 nm. Ultraviolet C light is considered to be the most effective light for disinfection. Within the ultraviolet C range, the most effective disinfection is considered to occur with radiation wavelengths between 248 nm and 262 nm.

With respect to the above description, it is to be realized that the optimum dimensional relationship for the various components of the invention described above and in FIGS. 1 through 6, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A dry cabinet disinfection system comprising:
a cabinet and an ultraviolet disinfection system;
wherein the dry cabinet disinfection system is designed for use by hair styling salons and barbershops;
wherein the dry cabinet disinfection system uses ultraviolet light for disinfecting a grooming tools used in hair styling salons and barbershops;
wherein the cabinet further comprises a box, a front frame, a door, a tray, a plurality of holes, a rubber molding, a wall mount, and one or more hinges.

2. The dry cabinet disinfection system according to claim 1 wherein the cabinet is a piece of furniture in the form of a rectangular block.

3. The dry cabinet disinfection system according to claim 2 wherein the cabinet is wall mounted.

4. The dry cabinet disinfection system according to claim 2 wherein
the cabinet is further defined with a first side, a second side, a third side, a fourth side, a fifth side, and a sixth side;
wherein the box is a single unit that forms the second side, the third side, the fourth side, the fifth side, and the sixth side of the cabinet.

5. The dry cabinet disinfection system according to claim 4 wherein
the front frame is a structural component attached to the sixth side of the box;
wherein the door is mounted on the front frame;
wherein the door is further defined with a first edge, a second edge, a third edge, and a fourth edge.

6. The dry cabinet disinfection system according to claim 5 wherein the edge of the door is formed with a plurality of semicircular cut outs.

7. The dry cabinet disinfection system according to claim 6 wherein the rubber molding is installed on the front frame near the door.

8. The dry cabinet disinfection system according to claim 7 wherein the tray is a shelf that is mounted inside the cabinet.

9. The dry cabinet disinfection system according to claim 8 wherein the tray has formed in it a plurality of holes.

10. The dry cabinet disinfection system according to claim 9 wherein the ultraviolet disinfection system is mounted in the interior of the cabinet.

11. The dry cabinet disinfection system according to claim 10 wherein the ultraviolet disinfection system further comprises a plurality of ultraviolet light sources, a door switch, a master switch and a plurality of ballasts.

12. The dry cabinet disinfection system according to claim 11 wherein each of the plurality of ultraviolet light sources comprises an ultraviolet c light bulb mounted in a ballast.

13. The dry cabinet disinfection system according to claim 12 wherein each individual combination of ballast and ultraviolet c light bulb is mounted in the interior of the cabinet in such a way that the interior of the cabinet is completely illuminated with ultraviolet c radiation.

14. The dry cabinet disinfection system according to claim 13 wherein operation of the each of the plurality of ballasts is controlled by a master switch, and a door switch.

15. The dry cabinet disinfection system according to claim 1 wherein the ultraviolet disinfection system is mounted in the interior of the cabinet.

16. The dry cabinet disinfection system according to claim 15 wherein the ultraviolet disinfection system further comprises a plurality of ultraviolet light sources, a door switch, a master switch and a plurality of ballasts.

17. The dry cabinet disinfection system according to claim 16 wherein each of the plurality of ultraviolet light sources comprises an ultraviolet c light bulb mounted in a ballast.

18. The dry cabinet disinfection system according to claim 17 wherein each individual combination of ballast and ultraviolet c light bulb is mounted in the interior of the cabinet in such a way that the interior of the cabinet is completely illuminated with ultraviolet c radiation.

19. The dry cabinet disinfection system according to claim 18 wherein operation of the each of the plurality of ballasts is controlled by a master switch, and a door switch.

* * * * *